US012605069B2

(12) United States Patent
Kokovidis et al.

(10) Patent No.: US 12,605,069 B2
(45) Date of Patent: Apr. 21, 2026

(54) SYSTEM HEALTH LIGHT SERVICE APP

(71) Applicant: Drägerwerk AG & Co. KGaA, Lübeck (DE)

(72) Inventors: Georgios Kokovidis, Waltham, MA (US); Kevin Thomas Jean, Pelham, NH (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 315 days.

(21) Appl. No.: 18/207,498

(22) Filed: Jun. 8, 2023

(65) Prior Publication Data

US 2023/0397815 A1      Dec. 14, 2023

Related U.S. Application Data

(60) Provisional application No. 63/350,617, filed on Jun. 9, 2022.

(51) Int. Cl.
A61B 5/00 (2006.01)

(52) U.S. Cl.
CPC .......... A61B 5/0022 (2013.01); A61B 5/7405 (2013.01)

(58) Field of Classification Search
CPC ............................ A61B 5/0022; A61B 5/7405
USPC ...................................................... 340/573.1
See application file for complete search history.

(56) References Cited

U.S. PATENT DOCUMENTS

| | | | |
|---|---|---|---|
| 11,364,837 B1 * | 6/2022 | Deyaf .................. | H05B 47/165 |
| 2002/0193925 A1 * | 12/2002 | Funkhouser ......... | G07C 5/0808 |
| | | | 701/31.8 |
| 2004/0016804 A1 * | 1/2004 | Namaky .............. | G07C 5/0816 |
| | | | 235/435 |
| 2005/0190069 A1 * | 9/2005 | Kemper .................. | G08B 1/08 |
| | | | 340/531 |
| 2009/0128325 A1 * | 5/2009 | Ivanov .................. | G16H 40/67 |
| | | | 340/539.12 |
| 2010/0023198 A1 * | 1/2010 | Hamilton ................ | B60R 16/03 |
| | | | 701/31.4 |
| 2018/0041377 A1 * | 2/2018 | Feltham .................. | H04W 4/80 |
| 2020/0235812 A1 * | 7/2020 | Saes ...................... | H04B 10/116 |
| 2021/0279657 A1 * | 9/2021 | Golden .................. | G01D 21/02 |
| 2021/0400476 A1 * | 12/2021 | Bendahan .......... | H04B 10/1141 |
| 2022/0402525 A1 * | 12/2022 | Maeda ............ | B60W 60/00188 |
| 2025/0055356 A1 * | 2/2025 | Sutton .................. | H02P 29/024 |

* cited by examiner

*Primary Examiner* — Omar Casillashernandez
(74) *Attorney, Agent, or Firm* — Nolte Lackenbach Siegel

(57) ABSTRACT

A system for transmitting a health status code from a first device that has no alpha-numeric display capability to a second device utilized by a service technician. The health status transmitted by a series of lights and/or sounds provided by the first device. Determining on the second device from the series of blinks or sounds the health status code transmitted by the first device. In some cases, decoding may include providing repair information to the service technician. In some cases, decoding may involve transmission from the second device to a remote computer and receipt of information pertaining to the decoding from the remote computer prior to presenting information to the service technician.

19 Claims, 7 Drawing Sheets

DEVICE

DIAGNOSTIC
MODULE
110

ENCODING
MODULE
120

LED CONTROL
MODULE
130

LIGHT EMITTING DIODE
("LED")
140

160

SERVICE DEVICE
(E.G., SMART PHONE — TABLET)

SERVICE
APPLICATION
150

CAMERA
175

170

145

300

IDENTIFY SYSTEM HEALTH — 305

ENCODE SYSTEM HEALTH — 310

TRANSMIT SIGNAL PATTERN
(AUDIBLE OR VISUAL) — 315

RECEIVE SIGNAL PATTERN — 320

DECODE SIGNAL PATTERN
(LOCAL OR REMOTE) — 325

DISPLAY ERROR CONDITION
(POSSIBLE CORRECTIVE ACTION) — 340

400

410

SYSTEM HEALTH LIGHT SERVICE APP

CROSS-REFERENCE TO RELATED APPLICATIONS

The priority and earlier effective filing date of U.S. Application Ser. No. 63/350,617, filed Jun. 9, 2022, is hereby claimed for all purposes, including the right of priority. This related application is also hereby incorporated by reference for all purposes as if expressly set forth verbatim herein.

TECHNICAL FIELD

The present disclosure generally relates to transmission of information wirelessly via optical (e.g., via light from a light emitting diode ("LED")) or audibly (e.g., via sound from a speaker). In particular, the disclosure relates to transmitting information regarding a device or system status using non-network and non-electronic transmissions.

BACKGROUND

This section of this document introduces information about and/or from the art that may provide context for or be related to the subject matter described herein and/or claimed below. It provides background information to facilitate a better understanding of the various aspects of the that which is claimed below. This is a discussion of "related" art. That such art is related in no way implies that it is also "prior" art. The related art may or may not be prior art. The discussion in this section of this document is to be read in this light, and not as admissions of prior art.

In the context of this disclosure, system health status refers to the diagnostic state of an electronic device. That is, a system with a "good" health status is expected to be performing within design criteria. In contrast, a system with "poor" or "bad" health status is performing in a degraded condition. Internal diagnostic modules of the device may monitor the device's operational performance and determine a health status for the overall device. In some cases, the diagnostic modules may be able to identify a particular component of the device that may be causing the degraded performance.

Many electronic devices include alpha-numeric displays for communicating the condition and/or health status of the device to users or service technicians (e.g., a person engaged in maintaining and/or repairing an electronic device). Such a display is typically capable of alerting for error conditions, providing statistics, providing diagnostic information, or the like. However, an informational display that provides alpha-numeric information may be a relatively expensive component for certain types of devices and may take up space on the device (both internally and on the exterior of the device).

Other devices allow for plugging in a cable to check the diagnostic status of a device. However, this type of implementation requires a cable and a port on the device for which to plug in the cable. Again, there is an added cost for both the cable and the port, and in some cases, an added inconvenience of needing a specific cable to perform the connection.

To address cost, usability, and size concerns, this disclosure presents an alternative technique for an electronic device to convey information about the operational state of the device itself. The disclosed techniques do not rely on alpha-numeric or even human readable displays on the device being diagnosed or on any communication ports on that device. A different technique, as described below, is used to convey the outbound information from the device being diagnosed. In contrast to existing techniques, disclosed techniques convey information from one device to another "reading device" via the wireless signaling techniques as described below.

BRIEF DESCRIPTION OF THE DRAWINGS

Illustrative embodiments of the subject matter claimed below will now be disclosed. In the interest of clarity, not all features of an actual implementation are described for every example in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

Figure 1:
FIG. 1 is a block diagram of a system including an electronic device and an associated electronic service device where the electronic device transmits system health information to the electronic service device according to one embodiment of the present disclosure.

While the invention is susceptible to various modifications and alternative forms, the drawings illustrate specific examples herein described in detail by way of example. It should be understood, however, that the description herein of specific examples is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Illustrative examples of the subject matter claimed below will now be disclosed. In the interest of clarity, not all features of an actual implementation are described for every example in this specification. It will be appreciated that in the development of any such actual implementation, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

Some electronic devices may have sufficient processing power for error detection but are not equipped to display, in a human-readable manner, information regarding the error condition or cause. Likewise, some electronic devices may lack communications processors that could enable the transfer, to other devices, of data related to device status or error conditions. For example, such devices may lack a microprocessor for communication with other devices via typical electronic communication methods such as network transmissions. Further, inclusion of the capability to provide electronic communication methods may increase the cost of manufacturing that electronic device. This disclosure provides techniques to include relatively low-cost components (e.g., LED or sound speaker) on the device and use those relatively low-cost components to convey information about the above-mentioned error detection.

According to various embodiments, an electronic device can be any electronic device capable of assessing status and/or error conditions and transmitting the same using an audible or visible signal. For example, an electronic device, configured to utilize the disclosed transmission techniques, may have a signal light or speaker that can provide a series of audible or visual signals to an associated electronic service device. In a simple case, the electronic device may provide a series of "blinks" or sounds that are received at the electronic service device and then decoded to determine an error condition.

The blinks or sounds (that represent a data signal) may, for example, be received by a camera or microphone (or combination thereof) at the electronic service device. Once received, the data signal may be processed locally on the service device, or the service device may be connected to a network and utilize devices on the network to assist in the decoding process. In some cases, it may be a combination of sounds and visual signals that are used to convey the information.

In one example, a sound may be used as a "synchronization" signal to indicate that a series of blinks is at its beginning. In this manner, the electronic service device may determine when to start a decoding process for the visual signals. In other cases, no speaker may be implemented. Accordingly, this type of implementation may utilize a different kind of synchronization such as a pause between flashes or a pre-defined series of quick flashes. Other synchronization techniques are also possible and, given the benefit of this disclosure, would be apparent to those in the art of signal transmission.

Embodiments of the present disclosure are directed to a system for enabling an electronic device to communicate its status, system health, error condition, and/or other information related to the device's functionality, to a service technician's computing device, for example a tablet or smart phone, which shall be referred to herein as the "electronic service device" or simply "service device." Such information regarding the electronic device functionality can be transmitted from the electronic device to the service technician's computing device via blinking codes emitted by a light emitting diode ("LED") or other light on the electronic device.

Disclosed systems and techniques utilize two different devices. A first of the two devices is the "electronic device" which is the device that is providing a diagnostic code via the audible or visual techniques disclosed herein. A second device is the electronic service device that "reads" the audible or visual information by utilizing a camera, speaker, or combination thereof. As a result, the components (e.g., LED, speaker, etc.) of the electronic device may be low-cost components while the electronic service device includes the components and intelligence (e.g., code executed by a processing device) to facilitate decoding the diagnostic information. As mentioned above, the decoding may be performed locally on the electronic service device or may be initiated by the electronic service device via transmission to other computing resources.

In other words, in accordance with this disclosure, information related to the electronic device can be encoded into a pattern, which pattern is then expressed by repeatedly activating and deactivating the light on the electronic device. A camera or other light-sensing device on the service device can detect this blinking pattern and decode it to determine the status information of the electronic device. The service device may then relay such information to the service technician in a human-readable form, such as text and/or graphical output on the service device display. The service technician can use the transmitted information regarding the electronic device to aid in the diagnosis, repair, and/or maintenance of the electronic device.

In the present disclosure, the term "service technician" may refer to a person engaged in servicing, maintaining, repairing, and/or troubleshooting or diagnosing an electronic device according to embodiments disclosed herein. As described herein, a service technician may use the service device as an aid in repairing or replacing the electronic device. In utilizing the disclosed techniques, the service technician may perform the diagnosis without establishing a wired connection or a conventional network connection between the service device and the electronic device.

According to one embodiment of the present disclosure, an electronic device may comprise virtually any type of machine or apparatus that has a computer processor and a computer-readable memory. Embodiments include one or more applications, such as software packages, modules, or systems, implemented on one or more computing systems.

As used herein, the term "computing system" includes, but is not limited to, a portable computing system; a smart phone; a mobile computing system; a laptop computing system; desktop computing system; a notebook computing system; a tablet computing system; a workstation; a server computing system; a mobile phone; a wireless telephone; an Internet appliance; a dedicated microprocessor; or any device that includes components that can execute all, or part, of any one of the processes and/or operations as described herein. In addition, as used herein, the term "computing system" can denote, but is not limited to, systems made up of multiple computing systems and set forth above and/or any devices that can be used to perform the processes and/or operations as described herein. A computing system can also denote logical computing, such as a group of atoms, computers, or other state tracking systems that perform calculations for purposes of acting as a computing platform.

Referring to FIG. 1, one embodiment of device health communication system 100 comprises, on the electronic device 160 that is to be diagnosed, diagnostic module 110, encoding module 120, LED control module 130, and LED 140. On the service device 170 there is illustrated service application 150 and camera 175. In this embodiment, dotted line 145 illustrates the communication between service device 170 and electronic device 160. As explained above, service device 170 may also include a microphone (not shown) while electronic device 160 may also include a speaker (not shown). Thus, dotted line 145 represents any type of communication in which audible and/or visual information is conveyed from electronic device 160 to service device 170 based on the techniques of this disclosure.

In one implementation, it is expected that electronic device 160 may be a medical device (e.g., heartrate monitor, glucose meter, or other type of measuring device) that may be too small to incorporate an alpha-numeric display but may include an LED for use with a corresponding service device 170. It is also envisioned that service device 170 may be a smartphone, tablet, or other type of portable computing or communication device that may be carried by a service technician and include a camera and/or a speaker and includes a processor to perform the capabilities described for service application 150.

Embodiments in accordance with the present disclosure may be embodied as an apparatus, method, or computer program product. Accordingly, the present disclosure may take the form of an entirely hardware-comprised embodiment (including pre-programmed logic modules), an entirely software-comprised embodiment (including firmware, resident software, micro-code, etc.), or an embodiment combining software and hardware aspects that may all generally be referred to herein as a "circuit," "module," or "system." Furthermore, embodiments of the present disclosure may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory ("RAM") device, a read-only memory ("ROM") device, an erasable programmable read-only memory ("EPROM" or Flash memory) device, an optical storage device, and a magnetic storage device. Computer program code for carrying out operations of the present disclosure may be written in any combination of one or more programming languages. Such code may be compiled from source code to computer-readable assembly language or machine code suitable for the device or computer on which the code will be executed.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service technician interaction and then scaled accordingly. A cloud model can be composed of various characteristics (e.g., on-demand self-service, broad network access, resource pooling, rapid elasticity, and measured service), service models (e.g., Software as a Service ("SaaS"), Platform as a Service ("PaaS"), and Infrastructure as a Service ("IaaS")), and deployment models (e.g., private cloud, community cloud, public cloud, and hybrid cloud).

According to various embodiments, the present disclosure is directed to systems and/or modules for detecting and/or logging a device condition in an electronic device, communicating the detected condition to a service device, interpreting the communicated condition at the service device, and displaying information regarding the detected condition to a service person.

In embodiments of the present disclosure, diagnostic module 110 comprises a memory storage containing computer-readable instructions and a processor capable of executing the computer-readable instructions. Embodiments of diagnostic module 110 are configured to identify any error condition, such as a malfunction and/or potential malfunction within electronic device 160. In embodiments, diagnostic module 110 is configured to determine one or more operating conditions of electronic device 160, compare the operating conditions to optimal parameters, and determine whether an error condition is present due to operating conditions being outside of design parameters.

In embodiments, diagnostic module 110 detects a runtime error that is raised by software and/or hardware during the operation of electronic device 160. In such cases, diagnostic module 110 may then ascertain the source of the runtime error and begin operation of LED 140 (and possibly an optional speaker) to convey information about that determined source. The operation of LED 140 may be performed collectively by encoding module 120 (which encodes the information to be "blinked" on the LED 140) and LED control module 130 (which activates the actual blinking code via the LED 140).

In some embodiments, diagnostic module 110 receives operating data from one or more sensors within, in, at, and/or near electronic device 160 or configured to otherwise detect one or more conditions of electronic device 160 that are relevant to the operation of electronic device 160. For example, in one embodiment, a sensor may comprise a thermocouple or other temperature sensing device adapted to transmit a measured temperature of electronic device 160 (or a specific component thereof) to diagnostic module 110. In this example, diagnostic module 110 compares the measured temperature against a target or optimal temperature, and if the measured temperature is above or below target temperature thresholds, diagnostic module 110 can determine that an alert condition is present. In other cases, other types of sensors may be utilized by diagnostic module 110 to determine the status of electronic device 160.

In embodiments of the present disclosure, encoding module 120 comprises a memory storage containing computer-readable instructions and a processor capable of executing the computer-readable instructions. Embodiments of encoding module 120 are configured to receive a signal from diagnostic module 110 regarding a condition of electronic device 160. The condition of electronic device 160 can include detected or potential errors, hardware or software malfunctions, or other information related to maintenance and/or diagnostics of electronic device 160.

Upon receiving a signal from diagnostic module 110 regarding electronic device 160, encoding module 120 may generate a signal pattern that corresponds to the detected condition of electronic device 160. In one embodiment, encoding module 120 comprises a lookup table that correlates a signal pattern for each potential condition or for predetermined error codes. In other embodiments, encoding module 120 is configured to translate the received signal into a signal pattern using a translation algorithm. Other techniques are also possible with the end result being that encoding module 120 determines information that is to be conveyed outside of electronic device 160.

In various embodiments, the signal pattern generated by encoding module 120 represents the condition of electronic device 160. In one embodiment, the signal pattern comprises a series of activations and deactivations of a light source. The duration of each activation, the color of each activation, the interval between each activation, and the quantity of activations can make up the signal pattern. In some embodiments, light intensity is a component of the signal pattern in cases where electronic device 160 has a light source with the ability to modulate its intensity. In some embodiments, sound may be used to accompany or synchronize activations of the light source.

In one embodiment, encoding module 120 can employ a standard communication protocol for transmitting data, for example a serial communication data transmission protocol. In one example embodiment, encoding module 120 uses data and control signals from the RS-232 standard to generate the signal pattern.

In some embodiments, encoding module 120 is adapted to store the signal pattern in a memory storage. In one embodiment, encoding module 120 transmits the generated signal pattern to LED control module 130. In one embodiment of the present disclosure, encoding module 120 can encrypt one or more error codes and/or other information to be transmitted to service application 150 executing on electronic service device 170, thereby generating an encrypted signal pattern.

In embodiments of the present disclosure, LED control module 130 comprises a memory storage containing computer-readable instructions and a processor capable of executing the computer-readable instructions. Embodiments of LED control module 130 are configured to direct LED 140 to activate in accordance with the signal pattern generated by encoding module 120. In some embodiments, LED control module 130 transmits an electrical signal to LED 140 at voltage levels to accommodate the specifications and particular forward operating voltage of LED 140. As LED 140 receives the electrical signal from LED control module 130, LED 140 illuminates, thereby flashing the encoded signal pattern. In some embodiments, LED 140 is substituted with other types of light-emitting devices.

In embodiments of the present disclosure, service application 150 is installed on service device 170 that is to be used by a service technician (not shown). According to embodiments, service device 170 comprises a memory storage containing computer-readable instructions and a processor capable of executing the computer-readable instructions. Embodiments of service application 150 comprise a software package installed on service device 170. Service application 150 may be configured to use camera 175 or other light-detecting sensor of service device 170, wherein camera 175 or light-detecting sensor is capable of sensing and identifying the coded signal pattern emitted by LED 140. Additionally, service application 150 may obtain input information representing audible information captured by a microphone of service device 170 and use that information in conjunction with the light-detection described.

According to one embodiment, the service technician interfaces with service device 170 to enter service application 150 into observation mode, wherein service application 150 activates camera 175. The service technician can then aim camera 175 at LED 140 as LED 140 emits the signal pattern. Service application 150 includes programming for detection of light emitted from LED 140 and possibly recognition of the signal pattern. According to some embodiments, service application 150 employs optical recognition methods to identify LED 140 and detect light emitted therefrom. According to some embodiments, service application 150 may include logic to decode and present information to the service technician directly from service device 170. In other implementations, service application 150 may transmit information externally from service device 170 and subsequently receive a response to the transmission prior to conveying information to the service technician.

According to one embodiment of the present disclosure, service application 150 can decode the received signal pattern to a human-readable form. In one embodiment, service application 150 includes a lookup table to translate the received signal pattern into an error code or status. In some embodiments, service application 150 can translate the received signal pattern into human-readable text or graphics according to a preselected decoding protocol that corresponds to the encoding protocol used by encoding module 120 to generate the signal pattern.

Embodiments of service application 150 are further programmed to display, to the service technician, the error code and/or status of electronic device 160. In various embodiments, electronic device 160 presents the foregoing information to the service technician in a way that enables the service technician to assess the condition of electronic device 160 and to apply maintenance and/or repair procedures to electronic device 160.

In one embodiment, service application 150 is configured to store additional instructions or other information related to diagnosis, maintenance, and/or repair procedures, which instructions or information can be displayed to the service technician. To this end, the implementation of the additional instructions and their functionality will depend on the implementation of the electronic device 160. That is because the functionality and design of each implementation of the electronic device 160 may vary, and, so then will the diagnosis and troubleshooting.

Such additional instructions or information may be selected for display to the service technician in response to the error code and/or status of electronic device 160, as indicated by the received signal pattern. Alternatively, such instructions or information may be recalled in response to a selection made by the service technician in service application 150. The recalled information may be obtained locally from service device 170 or may be obtained via a network connection from service device 170 to other external computing resources.

Figure 2:
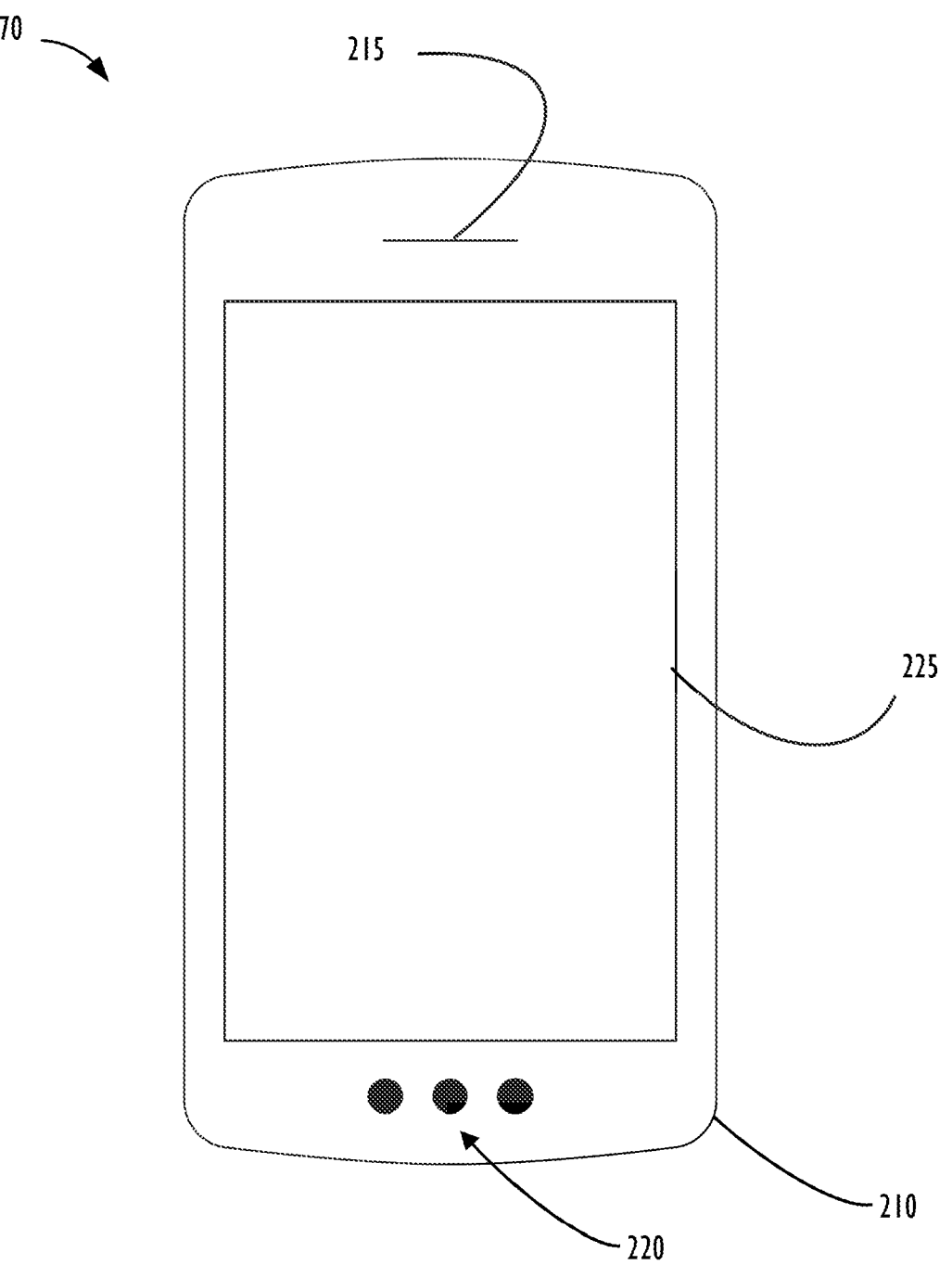
FIG. 2 is an electronic service device capable of receiving information regarding system health status from another electronic device according to an embodiment of the present disclosure.

Referring now to FIG. 2, one example implementation of service device 170 is illustrated. As shown, service device 170 may include a microphone 215, a user interface screen 225, and one or more optical sensing devices 220. Further, service device 170 may have a shell or cover such as housing 210 that provides protection for service device 170. User interface screen 225, in this example, is a touch screen that provides an input and output capability for a service technician. The one or more optical sensing devices 220 may be multiple instances of a camera such a camera 175 discussed above or may be multiple inputs to a single camera within service device 170. Internal to service device 170 and not shown may be processors, memory, network interfaces, and other components typical of a smartphone or tablet computer system.

Figure 3:
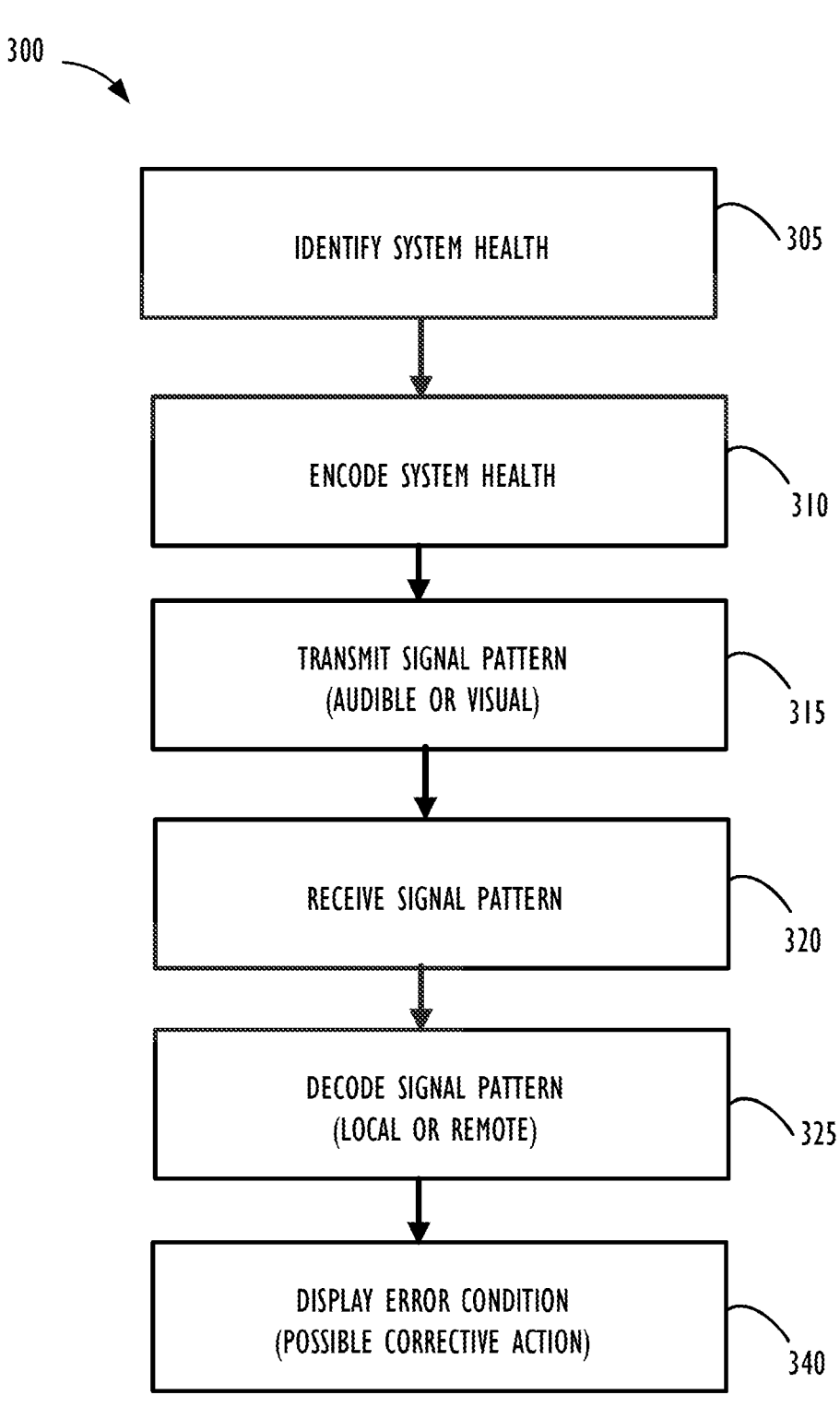
FIG. 3 is a flow chart depicting one method of transmitting system health information for the system illustrated in FIG. 1 according to one or more disclosed embodiments of the present disclosure.

Referring now to FIG. 3, method 300 is illustrated in flowchart form. Method 300 may be performed by the multiple devices illustrated for device health communication system 100 of FIG. 1 discussed above. As appropriate, different portions of method 300 may be performed on the different devices.

Method 300 begins at block 305 where an electronic device (e.g., electronic device 160 of FIG. 1) may identify its system health at block 305. For example, the electronic device may identify its system health by using a diagnostic module such as diagnostic module 110 discussed above for FIG. 1. For example, the electronic device may determine that it is functioning normally. As other examples, the electronic device may detect a fault in its hardware and/or software or a non-optimal condition that could indicate or lead to a malfunction. In one embodiment of identify system health, the electronic device conducts a routine system check and ascertains its operating condition during the system check. In another embodiment of identify system health, the electronic device detects a malfunction and/or a measurement outside its normal operating parameters and then determines an error condition as a result thereof.

Following identify system health at block 305, method 300 proceeds to encode system health at block 310. In embodiments of encode system health, the electronic device generates a signal pattern that represents the system health determined previously. In some embodiments, the electronic device incorporates additional metadata into the signal pattern. For example, the model and/or serial number, the age, any previous maintenance and/or repair activity, and the service life of the electronic device can be encoded and/or appended to the signal pattern.

According to one embodiment, the signal pattern comprises a blink code in which information relevant to the system health is encoded. A blink code may refer to a serial set of ON and OFF instructions, distributed over a predetermined interval of time that can later be decoded (e.g., by the electronic service device) to determine the system health.

In embodiments of encode system health, the electronic device is configured to use a lookup table to correlate the detected condition with a signal pattern uniquely assigned to that condition. In some embodiments, a binary translation protocol is used to convert an error code or status into a signal pattern that represents the condition of the electronic device.

Following encode system health at block 310, method 300 proceeds to transmit signal pattern (audible or visual) at block 315. In embodiments of transmit signal pattern, a light-emitting source (and/or a sound emitting source) on the electronic device is repeatedly activated and deactivated in succession according to the signal pattern generated in encode system health. According to various embodiments of the present disclosure, the light-emitting source comprises an LED. In one embodiment, following completion of the signal pattern, the transmission is repeated for a time duration while the electronic device still detects the condition.

Following transmit signal pattern at block 315, method 300 proceeds to receive signal pattern at block 320. In embodiments of receive signal pattern (which executes on the service device such as electronic service device 170 of FIGS. 1 and 2), the technician's service device has a camera or light-sensing apparatus that is aimed at the light-emitting source of the electronic device. The service device includes image recognition software configured to detect the signal pattern from the blinking light-emitting source. If implemented, sound patterns may accompany or replace the visual signaling.

Following receive signal pattern at block 320, method 300 proceeds to decode signal pattern at block 325. In embodiments of decode signal pattern, service device decodes the signal pattern to determine the electronic device status, including any error codes, as determined previously. In embodiments, the service device comprises a copy of the lookup table used by the electronic device at encode system health (block 310).

Following decode signal pattern at block 325, method 300 proceeds to display error condition at block 340. In embodiments of display error condition, the service device displays human-readable text and/or graphics to service technician regarding the status of the electronic device. For example, information may be presented through a user interface of service device 170 such as shown by user interface screen 225 of FIG. 2. In some embodiments of display error condition, the service device additionally displays instructions to treat an error or malfunction of the electronic device as diagnosed in identify system health (block 305). In some cases, the service device displays recommended maintenance steps for the technician to service the electronic device according to the age and/or service life of the electronic device.

Following display error condition at block 340, the service technician can carry out corrective action on the electronic device. In some embodiments of the present disclosure, information related to the status or system health of the electronic device is uploaded from the service device to a remote computer or server for further action and/or logging.

Figure 4:
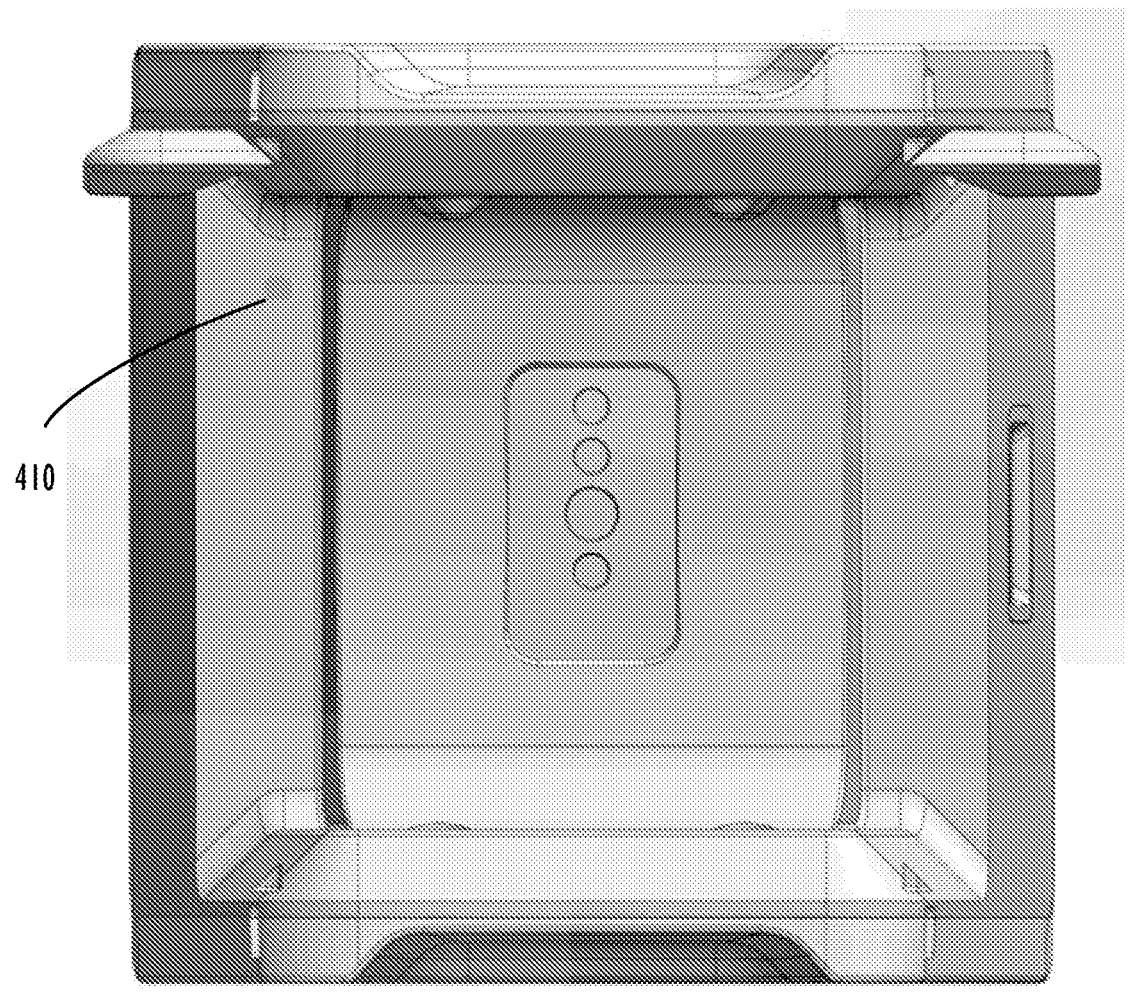
FIG. 4 is an example of an electronic device without any alpha-numeric display that includes an LED and/or speaker for signaling the internal health status of that device according to one or more disclosed embodiments of the present disclosure.

FIG. 4 depicts one example of an electronic device 400 that represents one example of electronic device 160 shown in FIG. 1 and discussed previously. In the embodiment depicted, electronic device 400 comprises LED 410. Electronic device 400 is configured to blink LED 410 according to a generated signal pattern that represents an error condition and/or status of electronic device 400. Notably, electronic device 400 does not have any type of alpha-numeric display incorporated into itself. Also, although not visible, electronic device 400 may include a speaker to provide audible signals that may be used in conjunction with or as a replacement for the visual signals provided by LED 410.

Figure 5:
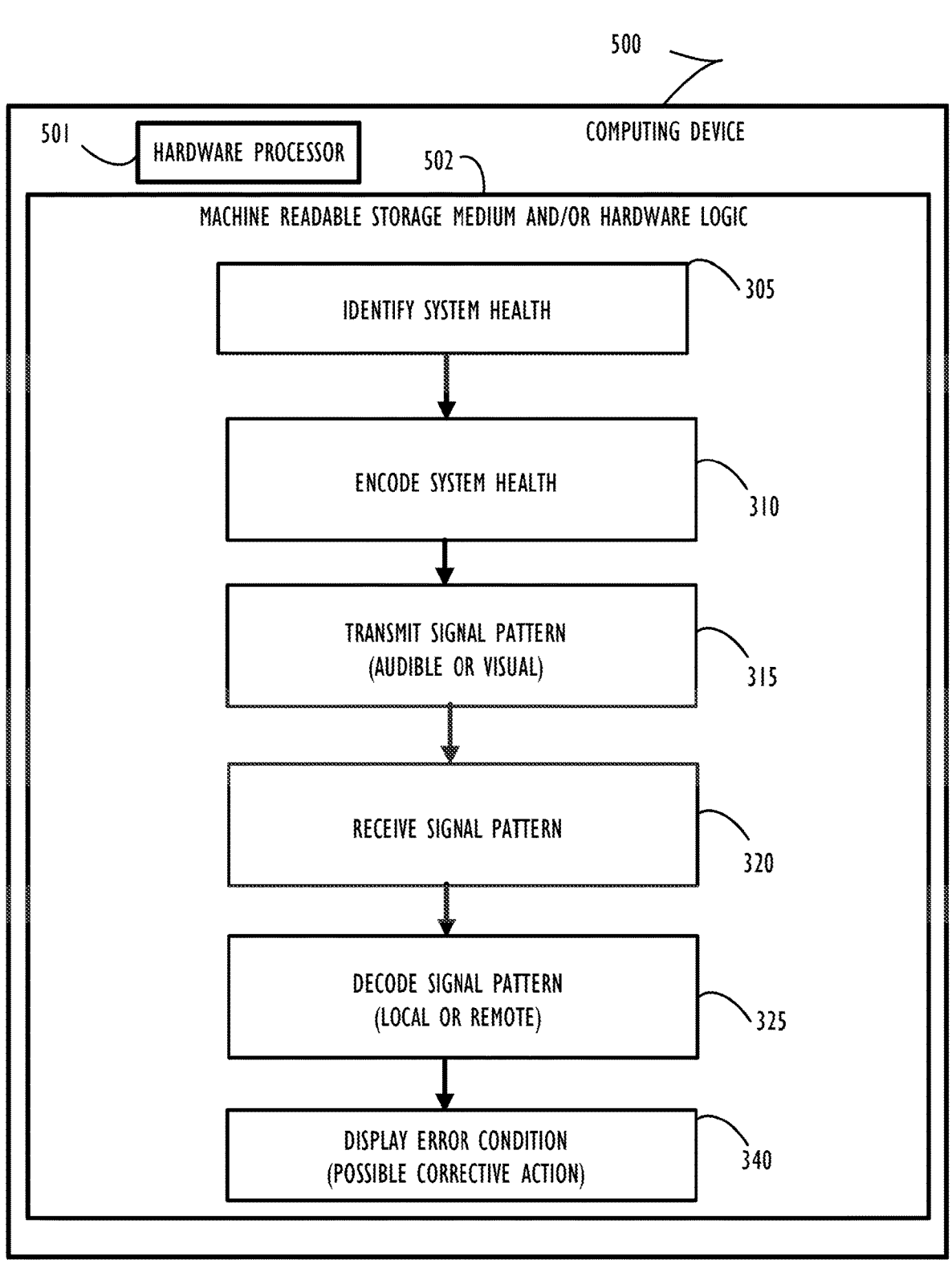
FIG. 5 is an example of a computing device, including a computer readable medium, that may be used to implement one or more of the workflows (in this case the workflow of FIG. 3) according to one or more examples of this disclosure.

Referring now to FIG. 5, shown is an example computing device 500, with a hardware processor 501, and accessible machine-readable instructions stored on a machine-readable medium and/or hardware logic 502 that may be used to perform one or more functions of the system health light service application, according to one or more disclosed example implementations. In the illustrated embodiment, element 502 is a machine-readable medium. Specifically, FIG. 5 illustrates computing device 500 configured to perform the example workflow of method 300 as an example. However, computing device 500 may also be configured to perform the flow of other methods, techniques, functions, or processes described in this disclosure. In this example of FIG. 5, machine-readable storage medium 502 includes instructions to cause hardware processor 501 to perform blocks 305-340 discussed above with reference to FIG. 3. Different implementations of method 300 are possible, including hardware logic configured on a chip to implement all or part of workflow 300 in conjunction with an overall implementation of disclosed techniques to provide a cloud-based lookup of information to implement disclosed embodiments.

A machine-readable storage medium, such as element 502 of FIG. 5, may include both volatile and nonvolatile, removable and non-removable media, and may be any electronic, magnetic, optical, or other physical storage device that contains or stores executable instructions, data structures, program module, or other data accessible to a processor, for example firmware, erasable programmable read-only memory ("EPROM"), random access memory ("RAM"), non-volatile random access memory ("NVRAM"), optical disk, solid state drive ("SSD"), flash memory chips, and the like. The machine-readable storage medium may be a non-transitory storage medium, where the term "non-transitory" does not encompass transitory propagating signals.

Figure 6:
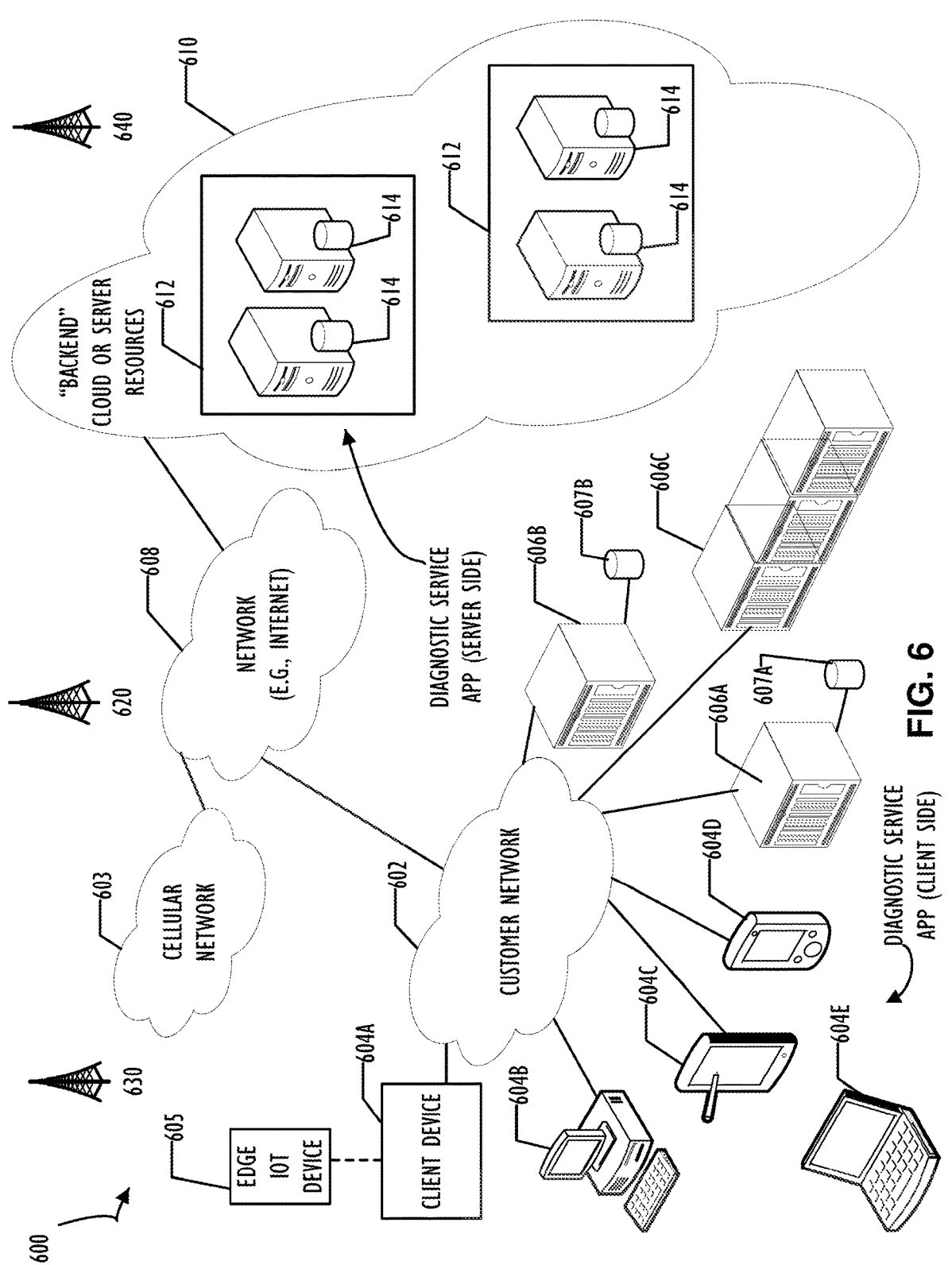
FIG. 6 is an example of a network infrastructure including networked computer components and devices to illustrate possible processing resources, user interface points, and data pathways, according to one or more examples of this disclosure.

FIG. 6 represents a network infrastructure 600 that may be used to implement all, or part of the disclosed system health light service application, according to one or more disclosed embodiments. Network infrastructure 600 includes a set of networks where embodiments of the present disclosure may operate. Network infrastructure 600 comprises a customer network 602 (which may represent a WiFi® network where service devices such as electronic service device 170 may be utilized), network 608 (which may be the Internet), cellular network 603, and a cloud service provider network 610. In one embodiment, customer network 602 may be a local private network, such as local area network ("LAN") that includes a variety of network devices that include, but are not limited to switches, servers, and routers.

Each of these networks can contain wired or wireless programmable devices and operate using any number of network protocols (e.g., Transmission Control Protocol/Internet Protocol, or "TCP/IP") and connection technologies (e.g., WiFi® networks, or Bluetooth®. In another embodiment, customer network 602 represents an enterprise network that could include or be communicatively coupled to one or more local area networks ("LANs"), virtual networks, data centers and/or other remote networks (e.g., 608, 610). In the context of the present disclosure, customer network 602 may include one or more high-availability switches or network devices using methods and techniques such as those described above. Specifically, compute resource 606B and/or compute resource 606A may be configured as a network infrastructure device incorporating storage devices (e.g., 607A and 607B). An enterprise customer network may be utilized if a corporation were to implement one or more embodiments of the present disclosure to assist with device diagnostics at a single large facility.

As shown in FIG. 6, customer network 602 may be connected to one or more client devices 604A-E and allow the client devices 604A-E to communicate with each other and/or with cloud service provider network 610, via network 608 (e.g., the Internet). Client devices 604A-E may be computing systems such as desktop computer 604B, tablet computer 604C, mobile phone 604D, laptop computer (shown as wireless) 604E, and/or other types of computing systems generically shown as client device 604A. In the examples of this disclosure, service technicians may obtain access to the diagnostic service application via a service device such as client devices 604A-E illustrated in network infrastructure 600.

Network infrastructure 600 may also include other types of devices generally referred to as Internet of Things ("IOT") (e.g., edge IOT device 605) that may be configured to send and receive information via a network to access cloud computing services or interact with a remote web browser application (e.g., to receive information or respond to requested information).

FIG. 6 also illustrates that customer network 602 includes local compute resources 606A-C that may include a server, access point, router, or other device configured to provide for local computational resources and/or facilitate communication amongst networks and devices. For example, local compute resources 606A-C may be one or more physical local hardware devices. Local compute resources 606A-C may also facilitate communication between other external applications, data sources (e.g., 607A and 607B), and services, and customer network 602.

Network infrastructure 600 also includes cellular network 603 for use with mobile communication devices. Mobile cellular networks support mobile phones and many other types of mobile devices such as laptops etc. Mobile devices in network infrastructure 600 are illustrated as mobile phone 604D, laptop computer 604E, and tablet computer 604C. A mobile device such as mobile phone 604D may interact with one or more mobile provider networks as the mobile device moves, typically interacting with a plurality of mobile network towers 620, 630, and 640 for connecting to the cellular network 603.

FIG. 6 illustrates that customer network 602 is coupled to a network 608. Network 608 may include one or more computing networks available today, such as other LANs, wide area networks ("WAN"), the Internet, and/or other remote networks, in order to transfer data between client devices 604A-D and cloud service provider network 610 (e.g., a cloud service provider hosting the disclosed home care management system application). Each of the computing networks within network 608 may contain wired and/or wireless programmable devices that operate in the electrical and/or optical domain.

In FIG. 6, cloud service provider network 610 is illustrated as a remote network (e.g., a cloud network) that is able to communicate with client devices 604A-E via customer network 602 and network 608. The cloud service provider network 610 acts as a platform that provides additional computing resources to the client devices 604A-E and/or customer network 602. In one embodiment, cloud service provider network 610 includes one or more data centers 612 with one or more server instances 614. Cloud service provider network 610 may also include one or more frames or clusters (and cluster groups) representing a scalable compute resource that may implement the techniques of this disclosure.

Figure 7:
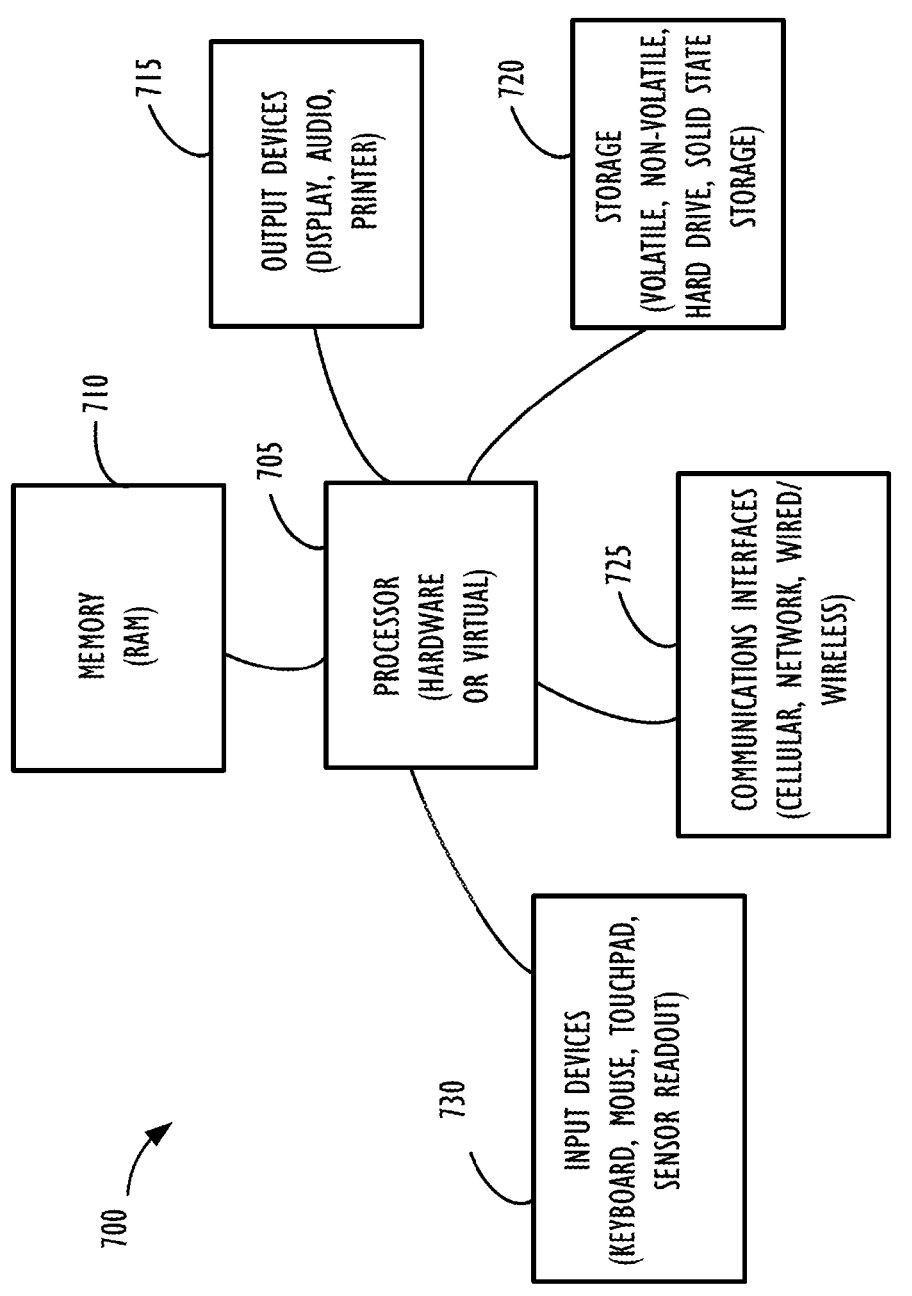
FIG. 7 is a block diagram providing an example of a computing device that may be used within one or more of the devices shown in FIG. 1, 4, or 6 (or even other devices).

FIG. 7 illustrates a computing device 700 that may be used to implement or be used with the functions, modules, processing platforms, execution platforms, communication devices, and other methods and processes of this disclosure. For example, computing device 700 illustrated in FIG. 7 could represent a client device or a physical server device and include either hardware or virtual processor(s) depending on the level of abstraction of the computing device. In some instances (without abstraction), computing device 700 and its elements, as shown in FIG. 7, each relate to physical hardware. Alternatively, in some instances one, more, or all of the elements could be implemented using emulators or virtual machines as levels of abstraction. In any case, no matter how many levels of abstraction away from the physical hardware, computing device 700 at its lowest level may be implemented on physical hardware.

As also shown in FIG. 7, computing device 700 may include one or more input devices 730, such as a keyboard, mouse, touchpad, or sensor readout (e.g., biometric scanner) and one or more output devices 715, such as displays, speakers for audio, or printers. Some devices may be configured as input/output devices also (e.g., a network interface or touchscreen display).

Computing device 700 may also include communications interfaces 725, such as a network communication unit that could include a wired communication component and/or a wireless communications component, which may be communicatively coupled to processor 705. The network communication unit may utilize any of a variety of proprietary or standardized network protocols, such as Ethernet®, TCP/

IP, to name a few of many protocols, to effect communications between devices. Network communication units may also comprise one or more transceiver(s) that utilize the Ethernet®, power line communication ("PLC"), WiFi®, cellular, and/or other communication methods.

As illustrated in FIG. 7, computing device 700 includes a processing element such as processor 705 that contains one or more hardware processors, where each hardware processor may have a single or multiple processor cores. Examples of processors that might be used in various embodiments include, but are not limited to, microprocessors, controllers, microcontrollers, central processing units ("CPUs"), co-processors (e.g., math co-processors), or even chipsets containing multiple processor devices. As mentioned above, each of the multiple processor cores may be paired with a task scheduler to facilitate implementations of this disclosure.

In one embodiment, the processor 705 may include at least one shared cache that stores data (e.g., computing instructions) that are utilized by one or more other components of processor 705. For example, the shared cache may be a locally cached data stored in a memory for faster access by components of the processing elements that make up processor 705. In one or more embodiments, the shared cache may include one or more mid-level caches, such as level 2 ("L2"), level 3 ("L3"), level 4 ("L4"), or other levels of cache, a last level cache ("LLC"), or combinations thereof. Examples of processors include but are not limited to a central processing unit ("CPU") a microprocessor. Although not illustrated in FIG. 7, the processing elements that make up processor 705 may also include one or more of other types of hardware processing components, such as graphics processing units ("GPU"), application specific integrated circuits ("ASICs"), field-programmable gate arrays ("FPGAs"), and/or digital signal processors ("DSPs").

FIG. 7 illustrates that memory 710 may be operatively and communicatively coupled to processor 705. Memory 710 may be a non-transitory medium configured to store various types of data. For example, memory 710 may include one or more storage devices 720 that comprise a non-volatile storage device and/or volatile memory. Volatile memory, such as random-access memory ("RAM"), can be any suitable non-permanent storage device. The non-volatile storage devices 720 can include one or more disk drives, optical drives, solid-state drives ("SSDs"), tap drives, flash memory, read only memory ("ROM"), and/or any other type of memory designed to maintain data for a duration of time after a power loss or shut down operation. In certain instances, the non-volatile storage devices 720 may be used to store overflow data if allocated RAM is not large enough to hold all working data. The non-volatile storage devices 720 may also be used to store programs that are loaded into the RAM when such programs are selected for execution.

Persons of ordinary skill in the art are aware that software programs may be developed, encoded, and compiled in a variety of computing languages for a variety of software platforms and/or operating systems and subsequently loaded and executed by processor 705. In one embodiment, the compiling process of the software program may transform program code written in a programming language to another computer language such that the processor 705 is able to execute the programming code. For example, the compiling process of the software program may generate an executable program that provides encoded instructions (e.g., machine code instructions) for processor 705 to accomplish specific, non-generic, particular computing functions.

After the compiling process, the encoded instructions may then be loaded as computer executable instructions or process steps to processor 705 from storage device 720, from memory 710, and/or embedded within processor 705 (e.g., via a cache or on-board ROM). Processor 705 may be configured to execute the stored instructions or process steps in order to perform instructions or process steps to transform the computing device into a non-generic, particular, specially programmed machine or apparatus. Stored data, e.g., data stored by a storage device 720, may be accessed by processor 705 during the execution of computer executable instructions or process steps to instruct one or more components within the computing device 700.

A user interface (e.g., output devices 715 and input devices 730) can include a display, positional input device (such as a mouse, touchpad, touchscreen, or the like), keyboard, or other forms of user input and output devices. The user interface components may be communicatively coupled to processor 705. When the output device is or includes a display, the display can be implemented in various ways, including by a liquid crystal display ("LCD") or a cathode-ray tube ("CRT") or light emitting diode ("LED") display, such as an organic light emitting diode ("OLEO") display. Persons of ordinary skill in the art are aware that the computing device 700 may comprise other components well known in the art, such as sensors, powers sources, and/or analog-to-digital converters, not explicitly shown in FIG. 7.

Certain terms have been used throughout this description and claims to refer to particular system components. As one skilled in the art will appreciate, different parties may refer to a component by different names. This document does not intend to distinguish between components that differ in name but not function. In this disclosure and claims, the terms "including" and "comprising" are used in an open-ended fashion, and thus should be interpreted to mean "including, but not limited to . . . ." Also, the term "couple" or "couples" is intended to mean either an indirect or direct wired or wireless connection. Thus, if a first device couples to a second device, that connection may be through a direct connection or through an indirect connection via other devices and connections. The recitation "based on" is intended to mean "based at least in part on." Therefore, if X is based on Y, X may be a function of Y and any number of other factors.

The flowcharts and block diagram in the attached figures illustrate the architecture, functionality, and operation of possible implementations of systems, methods, and computer program products according to various embodiments of the present disclosure. In this regard, each block in the flowcharts or block diagram may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowcharts and/or block diagram block or blocks.

The phrase "configured to" takes on the meaning that those ordinarily skilled in the art would assign to it. More particularly, the phrase "configured to" means that what ever component that is "configured to" perform some task of function has been designed and implemented to perform that task. For example, a processor may be "configured to" perform some task by programming it to do so. Similarly, a circuit or other piece of hardware may be "configured to" perform some function by being designed and implemented to do so.

This concludes the detailed description. The particular examples disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular examples disclosed above may be altered or modified and all such variations are considered within the scope and spirit of the invention. Accordingly, the protection sought herein is as set forth in the claims below.

What is claimed is:

1. An electronic device that contains no alpha-numeric display capability, the electronic device comprising:
a diagnostic module configured to determine a health status of the electronic device,
an encoding module configured to generate a signal pattern based on the health status,
a light emitting diode ("LED"), and
an LED control module configured to direct the LED to sequentially activate multiple times according to the signal pattern,
wherein the electronic device visually communicates with an electronic service device that contains no electronic transmission coupling to the electronic device, the communication occurring when initiated by the electronic service device by reading the sequential activation to decode the signal pattern into a diagnostic code for presentation on an alpha-numeric display of the electronic service device;
wherein a synchronization signal indicates a beginning of transmission of the signal pattern.

2. The electronic device of claim 1, wherein the encoding module is adapted to encrypt the health status, thereby resulting in the signal pattern.

3. The electronic device of claim 1, wherein the electronic device comprises a medical device.

4. The electronic device of claim 1, wherein;
the electronic device includes a sound speaker to emit an audible signal as part of a diagnostic signal including the signal pattern; and
the LED is configured to emit the signal pattern in conjunction with the audible signal.

5. The electronic device of claim 1, wherein the electronic service device comprises a smart phone or a tablet computer device.

6. The electronic device of claim 1, wherein the synchronization signal is an audible sound.

7. The electronic device of claim 1, wherein the synchronization signal is a pause for a pre-determined period of time between visual signals or a pre-determined sequence of visual signals that do not have encoded information.

8. The electronic device of claim 1, wherein the signal pattern is decoded locally on the electronic service device or remotely on remote computing resources.

9. A method of conveying information from a first electronic device that has no alpha-numeric display to a second electronic device that is not electronically coupled to the first electronic device, the method comprising:
generating a diagnostic signal on the first electronic device, the diagnostic signal including a visual signal;
receiving the diagnostic signal on the second electronic device via a camera of the second electronic device;
decoding the received diagnostic signal to obtain a health status indication of the first electronic device; and
presenting on an alpha-numeric display of the second electronic device information providing the health status indication of the first electronic device;
wherein a synchronization signal indicates a beginning of transmission of the signal pattern.

10. The method of claim 9, wherein decoding the diagnostic signal includes:
transmitting the received diagnostic signal from the second electronic device to a remote computer system; and
receiving a response from the remote computer system prior to presenting the health status indication of the first electronic device.

11. The method of claim 9, wherein:
the diagnostic signal includes an audible signal; and
receiving the diagnostic signal on the second electronic device includes receiving the diagnostic signal via a microphone of the second electronic device.

12. The method of claim 9, wherein the first electronic device is a medical device.

13. The method of claim 9, wherein the second electronic device is a smart phone or a tablet computer device.

14. A system, comprising:
a first electronic device having no alpha-numeric display capability, the first electronic device programmed to:
determine a health status of the first electronic device;
generate a signal pattern in which is encoded the health status; and
communicate the signal pattern; and a second electronic device including an alpha-numeric display, the second electronic device programmed to:
receive the communicated signal pattern; decode the signal pattern to obtain the health status of the first device; and
present the health status of the first electronic device on the alpha-numeric display of the second electronic device;
wherein a synchronization signal indicates a beginning of transmission of the signal pattern.

15. The system of claim 14, wherein the first electronic device comprises:
a diagnostic module configured to determine the health status of the electronic device,
an encoding module configured to generate the signal pattern based on the health status,
a light emitting diode ("LED"), and
an LED control module configured to direct the LED to sequentially activate multiple times according to the signal pattern.

16. The system of claim 14, wherein the second electronic device is programmed to decode the diagnostic signal by:
transmitting the received diagnostic signal from the second electronic device to a remote computer system; and
receiving a response from the remote computer system prior to presenting the health status indication of the first electronic device.

17. The system of claim 14, wherein:
the first electronic device includes a sound speaker;

the diagnostic signal includes an audible signal;
the second electronic device includes a microphone; and
the second electronic device is programmed to receive the audible signal via the microphone.

18. The system of claim 14, wherein:
the first electronic device is a medical device; and
the second electronic device is a smart phone or a tablet computer device.

19. The system of claim 14, wherein the second electronic device is programmed to communicate the signal pattern visually, auditorily, or a combination thereof.

\* \* \* \* \*